United States Patent
Tufvesson et al.

(10) Patent No.: US 12,297,600 B2
(45) Date of Patent: May 13, 2025

(54) FLUFF PULP

(71) Applicant: Stora Enso OYJ, Helsinki (FI)

(72) Inventors: Helena Tufvesson, Gävle (SE); Marianne König, Stockholm (SE); Gunilla Söderstam, Stockholm (SE); Antonina Munguia-Chang, Gävle (SE)

(73) Assignee: Stora Enso OYJ, Helsinki (FI)

( * ) Notice: Subject to any disclaimer, the term of this patent is extended or adjusted under 35 U.S.C. 154(b) by 407 days.

(21) Appl. No.: 17/753,448

(22) PCT Filed: Sep. 3, 2020

(86) PCT No.: PCT/IB2020/058188
§ 371 (c)(1),
(2) Date: Mar. 3, 2022

(87) PCT Pub. No.: WO2021/044321
PCT Pub. Date: Mar. 11, 2021

(65) Prior Publication Data
US 2022/0290376 A1  Sep. 15, 2022

(30) Foreign Application Priority Data
Sep. 4, 2019  (SE) .................................. 1951006-4

(51) Int. Cl.
| D21H 27/00 | (2006.01) |
| A61F 13/15 | (2006.01) |
| D21C 3/02 | (2006.01) |
| D21C 9/00 | (2006.01) |
| D21C 9/147 | (2006.01) |
| D21H 11/16 | (2006.01) |
| D21H 15/04 | (2006.01) |
| A61F 13/53 | (2006.01) |

(52) U.S. Cl.
CPC ........... *D21H 27/007* (2013.01); *A61F 13/15* (2013.01); *D21C 3/02* (2013.01); *D21C 9/007* (2013.01); *D21C 9/147* (2013.01); *D21H 11/16* (2013.01); *D21H 15/04* (2013.01); *A61F 2013/530007* (2013.01)

(58) Field of Classification Search
CPC ...... D21H 27/007; D21H 11/16; D21H 15/04; A61F 13/15; A61F 2013/530007; D21C 3/02; D21C 9/007; D21C 9/147
See application file for complete search history.

(56) References Cited

U.S. PATENT DOCUMENTS

| 4,004,967 A | 1/1977 | Swan et al. |
| 5,164,043 A | 11/1992 | Griggs et al. |
| 5,536,369 A | 7/1996 | Norlander |
| 6,340,408 B1 * | 1/2002 | Norlander ............... A61L 15/60 162/25 |
| 10,106,927 B2 | 10/2018 | Nonni et al. |
| 2002/0096276 A1 * | 7/2002 | Leithem .................. D21C 9/004 162/90 |
| 2012/0325421 A1 | 12/2012 | Li et al. |
| 2014/0041817 A1 | 2/2014 | Sealey et al. |
| 2016/0040362 A1 | 2/2016 | Nonni et al. |
| 2018/0155875 A1 | 6/2018 | Ankerfors et al. |
| 2019/0174794 A1 | 6/2019 | Minohara et al. |

FOREIGN PATENT DOCUMENTS

| CL | 042589 | 9/1998 |
| CL | 58188 | 3/2017 |
| CN | 102459754 A | 5/2012 |
| CN | 103850145 A | 6/2014 |
| CN | 108193539 A | 6/2018 |
| GB | 1519072 | 7/1978 |
| JP | 2015151655 A | 8/2015 |
| JP | 2015198653 A | 11/2015 |
| WO | 9739188 | 10/1997 |
| WO | 2014026188 A1 | 2/2014 |

OTHER PUBLICATIONS

H. Melo, Desarrollos Tecnologicos Relevantes Para La Industria De Pulpa Y Papel, (1987), https://doi.org/10.52904/20.500.12220/6586.
Chilean Office action from corresponding Chilean patent application No. 2022-00384, dated Jul. 6, 2023.
International Search Report from corresponding PCT application No. PCT/IB2020/058188, mailed on Sep. 30, 2020.
Supplementary European Search Report from corresponding European application No. EP 20 86 1528 completed Jul. 20, 2023.
Zhisheng Hou, Basic Questions and Answers of Pulp and Paper, China Light Industry Press, Feb. 1992, pp. 70-73.
Office Action from corresponding Chinese patent application No. 202080061389.4, issued on Oct. 16, 2023.
Desarrollos Tecnologicos Relevantes Para La Industria De Pulpa Y Papel, by H. Melo (1987), https://doi.org/10.52904/20.500.12220/6586.

* cited by examiner

*Primary Examiner* — Jacob T Minskey
*Assistant Examiner* — Stephen M Russell
(74) *Attorney, Agent, or Firm* — Greer, Burns & Crain, Ltd.

(57) ABSTRACT

The present invention is directed to fluff pulp having a Kappa number in the range of from 5 to 18 and having, when in the form of a dry sheet, ISO brightness in the range of from 30 to 60% and having a specific volume in the dry defibrated state of at least 19 dm3/kg and having absorption time in the range of from 2 to 4 seconds.

11 Claims, No Drawings

FLUFF PULP

This application is a U.S. National Phase under 35 U.S.C. § 371 of International Application No. PCT/IB2020/058188, filed Sep. 3, 2020, which claims priority under 35 U.S.C. §§ 119 and 365 to Swedish Application No. 1951006-4 filed Sep. 4, 2019.

FIELD OF THE INVENTION

The present invention is directed to a fluff pulp having a Kappa number in the range of from 5 to 18 and having, when in the form of a dry sheet, ISO brightness in the range of from 30 to 60% and having a specific volume in the dry defibrated state of at least 19 $dm^3/kg$ and having absorption time in the range of from 2 to 4 seconds. The invention is also directed to a process for producing such fluff pulp and to the use thereof.

BACKGROUND

Fluff pulp is commonly made from softwood pulp from sulphate pulping. Depending on the pulping method, the properties of fluff pulp differs. Raw materials for softwood pulp may be various softwood species, such as Scandinavian pine, spruce, Southern pine, Loblolly pine, slash pine, Radiata pine, Douglas fir, Hemlock Cedar, White spruce, Lodgepole pine, Alpine fir or mixtures thereof.

Bleaching is a common method for removing lignin and colored compounds left after the pulp cooking and thereby increasing the brightness of pulp, including fluff pulp. Industry practice for improving appearance of fluff pulp is to bleach the pulp to desired of brightness (the Technical Association of the Pulp & Paper Industry ("TAPPI") or the International Organization for Standardization ("ISO")). The final ISO brightness of bleached pulps is between 85-94%. However, bleaching is expensive, represents a significant load on the environment and is often a source of manufacturing bottleneck.

Pulp is bleached or delignified in sequences and several bleaching steps and several bleaching chemicals need to be used to reach the desired brightness level. Examples of bleaching chemicals are oxygen, hydrogen peroxide, ozone, peracetic acid and chlorine dioxide.

In view of the production cost, resource requirement and environmental impact of bleaching, it would be desirable to able to achieve adequate fluff pulp properties, in particular sufficient absorption, but use less resources.

SUMMARY OF THE INVENTION

The present invention is directed to fluff pulp having a Kappa number in the range of from 5 to 18 and having, when in the form of a dry sheet, ISO brightness in the range of from 30 to 60% and having a specific volume in the dry defibrated state of at least 19 $dm^3/kg$ and having absorption time in the range of from 2 to 4 seconds.

It has surprisingly been found that fluff pulp with adequate properties can be produced with significantly less use of resources, in particular less use of chemicals and energy.

The present invention is also directed to a method to produce said fluff pulp.

The present invention is also directed to the use of said fluff pulp. The fluff pulp is produced and delivered to customers in the form of rolls. The fluff pulp is first defibrated. The defibrated pulp is then used in the manufacture of for example absorption cores for hygiene products and in airlaid-nonwoven for various applications such as diapers, incontinence products, feminine hygiene products etc.

DETAILED DESCRIPTION

As used herein, the term, "fluff" means defibrated, i.e. fiberized or shredded fluff pulp.

As used herein, the term "Kappa number" refers to measurement of Kappa number according to the standard ISO 302:2015.

The Kappa number of the fluff pulp according to the present invention is in the range of from 5 to 18, preferably in the range of 5 to 15, such as in the range of 6 to 15, more preferably in the range of from 5 to 12 or from 9 to 13.

As used herein, the term "ISO Brightness" refers to measurement of brightness according to the ISO standard 2470.

The ISO Brightness of the fluff pulp according to the present invention, when in the form of a dry sheet (i.e. before defibration), is in the range of from 30 to 60%, preferably in the range of from 35 to 55% or from 30 to 40%, more preferably in the range of from 36 to 50% or from 34 to 39%.

As used herein, the specific volume of the fluff (i.e. after defibration of the fluff pulp, i.e. in the defibrated state) in the dry state, refers to the specific volume determined according to the standard SCAN-C 33:80, which involves the determination of the volume of a test specimen in dry state per mass unit (weight) of fluff. A 3 g fluff sample, 50 mm in diameter, is formed in a forming unit. The sample is placed in the sample holder and a load of 2.8 kPa is applied. The specific dry volume is measured after 30 seconds (average of 5 replicates).

The specific volume in the dry state of the fluff (conditioned according to ISO187) according to the present invention is at least 19 $dm^3/kg$, preferably in the range of from 19 to 23 $dm^3/kg$, such as from 19 to 22 $dm^3/kg$.

As used herein, the term "absorption time" refers to the absorption properties of fluff pulp according to the standard SCAN-C 33:80, which involves the determination of the time consumed to completely saturate a standardized test specimen with absorbed liquid. A 3 g fluff sample, 50 mm in diameter, is formed in a forming unit. The sample is placed in a sample holder and a load of 2.8 kPa is applied. Tap water (23° C.) is applied underneath and the time required for the water to reach the top of the sample is recorded (average of 5 replicates).

As used herein, the term "absorption capacity" refers to the absorption capacity properties of fluff pulp according to the standard SCAN-C 33:80. A 3 g fluff sample, 50 mm in diameter, is formed in a forming unit. The sample is placed in the sample holder and a load of 2.8 kPa is applied. Tap water (23° C.) is applied underneath and the time required for the water to reach the top of the sample is recorded. After 30 seconds the addition of water stops. After additional 30 seconds the absorption capacity is recorded by measuring the weight of the test piece (average of 5 replicates).

As used herein, the "knot content" of the fluff pulp refers to the knot content measured by using Alpine Air Jet with screen DIN ISO 3310 1.4 mm. A sample of fluff is agitated for 10 minutes above a wire using 4000 kPa negative pressure. The knots remaining on the wire are weighed and reported as a percentage of the total sample weight (average of two replicates).

The knot content of the fluff pulp according to the present invention is preferably less than 13%.

The fluff pulp according to the present invention can be produced by the steps of
- a) preparing sulphate pulp;
- b) washing, screening and cleaning the pulp;
- c) subjecting the pulp to oxygen delignification;
- d) washing the pulp that has been subjected to oxygen delignification and optionally adjusting the pH of the pulp;
- e) drying the pulp to obtain fluff pulp, having a moisture content of less than 10 weight-%, in the form of a roll.

The pulp is sulphate pulp (Kraft pulp). The fibers of the fluff pulp according to the present invention preferably originate from softwood such as spruce and/or pine. Preferably, the sulphate pulp originates to at least 90% from softwood, less than 10% hardwood has been used in the preparation of the sulphate pulp. Thus, the sulphate pulp mainly originates from softwood but may contain traces of hardwood. The length-weighted average fiber length (measured on Metso Pulp Expert) is preferably in the range of from 1.8 to 2.5 mm, such as 1.9 to 2.2 mm. The pulp is washed, screened and cleaned before being subjected to the oxygen delignification step.

The oxygen delignification step is carried out using methods known in the art and can be carried in one or multiple steps. The pulp of is subjected to the oxygen delignification step in a wet state. Preferably the oxygen delignification is carried out until the pulp subjected to oxygen delignification has reached a Kappa number in the range of from 5 to 18.

The pulp that has been subjected to oxygen delignification is washed. The washing is typically carried out using water and may be carried out in one or more steps and may involve filtration. As part of the washing or immediately after the washing step, the pH may be adjusted. Preferably, the pH of the washed pulp should in the range of from 5 to 8, such as from 5 to 7. The washed pulp preferably contains less than 0.5 weight-% (based on the solids) extractives, more preferably less than 0.2 weight-% extractives, even more preferably less than 0.1 weight-% extractives and most preferably less than 0.05 weight-% extractives. In this context, extractives are for examples resins and fatty acids.

Optionally, hydrogen peroxide may be added to the washed pulp prior to the drying step.

The washed pulp is dried on a drying machine using methods known in the art. The dry pulp is formed into rolls after drying. The dried material has a moisture content of less than 10 weight-% (ISO 287), preferably less than 9%, such as in the range of from 6 to 9 weight-%.

Preferably, the fluff pulp according to the present invention has not been subjected to bleaching. More preferably, the fluff pulp according to the present invention has not been subjected to ECF (elemental chlorine free) or TCF (totally chlorine free) bleaching.

The fluff pulp may be treated with aluminum sulphate solution and pH adjusted to 5.5 to 6.5 in the stock preparation of the drying machine to decrease the defibration energy and knot content. The treatment has minor effect on absorption properties.

The fluff (i.e. the defibrated form of the fluff pulp) according to the present invention can be used in articles and products wherein fluff is typically used. Thus, the fluff can be used in absorption cores in baby diapers, incontinence products and feminine hygiene products. The fluff is also the main component in airlaid nonwoven.

Thus, the fluff pulp according to the present invention can, following defibration, for example be used in absorption cores and in airlaid nonwovens. It can be used as or in a liquid absorption material such as in absorbents in diapers, such as baby diapers as well as incontinence products. It can also be used for example in napkins and tissues. Such products can be produced using methods known in the art. The products typically comprise one or more further components, such as superabsorbents, polymers, wetting agents, viscose/rayon/lyocell fibers, bicomponent fibre, cotton fiber, other fibers, standard latex binder, specialty latex binder etc.

EXAMPLES

Example 1

Kraft pulp samples were collected from immediately after a production-scale pulp digester ("unbleached"), after a subsequent step of oxygen delignification ("oxygen delignified") and after a bleaching step ("bleached"). Thus, the "bleached" sample had been subjected to both oxygen delignification and bleaching.

Each pulp sample was rinsed thoroughly with water, centrifuged, granulated and stored in a fridge prior to analysis.

Laboratory sheets were formed from each type of pulp. The laboratory sheets were defibrated using a laboratory hammer mill (Kamas H01).

Chemical and fluff properties were tested according to the standard test methods. The results obtained are illustrated in table 1. The Kappa number was measured on the dry sheet formed. The ISO Brightness was measured on the dry sheet formed. The specific volume, absorption time and absorption capacity were measured on the fluffed material, i.e. after defibration. The sheet and pulp properties were evaluated in conditioned climate according to ISO 187.

TABLE 1

| | Chemical and fluff properties | | | | |
|---|---|---|---|---|---|
| Sample | Kappa number | ISO Brightness, % | Specific volume, dry state, dm³/kg | Absorption time, s | Absorption capacity, g/g |
| Unbleached | 25 | 24 | 22 | 10.5 | 10.0 |
| Oxygen delignified | 11 | 36 | 20.5 | 3 | 9.2 |
| Bleached | 1 | 87 | 21 | 2.5 | 9.5 |

It can be seen from the results reported in table 1 that the absorption properties as well as fluff properties (specific volume) are almost identical for the bleached fluff pulp as compared to the oxygen delignified fluff pulp.

Example 2

Kraft pulp samples were collected from immediately after a production-scale subsequent step of oxygen delignification ("oxygen delignified") and after a bleaching step ("bleached"). Thus, the "bleached" sample had been subjected to both oxygen delignification and bleaching.

Then the pulp was centrifuged, granulated and stored in dark plastic bags in refrigerator at 25 to 30% dry content. Pulp for one sheet was soaked and wet disintegrated. The pulp suspension was pH adjusted to 5.8, agitated for 10 minutes and then dewatered in a sheet former. Some of the samples were treated with $Al_2(SO_4)_3$, solution and then pH-adjusted with NaOH to 5.8.

The wet sheets were pressed and dried to a moisture content of <7%.

Chemical and fluff properties were tested according to the standard test methods. The results obtained are illustrated in table 1. The Kappa number was measured on the dry sheet formed. The ISO Brightness was measured on the dry sheet formed. The specific volume, absorption time and absorption capacity were measured on the fluffed material, i.e. after defibration. The sheet and pulp properties were evaluated in controlled climate conditions according to ISO 187.

TABLE 2

Chemical and fluff properties

| Sample | $Al_2(SO_4)_3$ solution, l/BDt | Kappa number | ISO Brightness, % | Specific volume, dry state, dm³/kg | Absorption time, s | Absorption capacity, g/g |
|---|---|---|---|---|---|---|
| Oxygen delignified | 0 | 9 | 39 | 22 | 3.2 | 9.4 |
| Oxygen delignified | 30 | 9 | 41 | 22 | 3.1 | 9.8 |
| Oxygen delignified | 45 | 9 | 40 | 22 | 3.1 | 9.8 |
| Oxygen delignified | 80 | 9 | 40 | 22 | 2.6 | 9.2 |
| Bleached | 30 | 1 | 86 | 21 | 2.3 | 9.7 |
| Bleached | 80 | 1 | 86 | 22 | 2.6 | 9.9 |

It can be seen from the results reported in table 2 that the absorption properties as well as fluff properties (specific volume) are almost identical for the bleached fluff pulp as compared to the oxygen delignified fluff pulp. The treatment with aluminum sulphate solution has minor effect on the absorption properties.

Example 3

A production trial was performed on a sulphate pulp fiber line with a drying machine for fluff pulp. The sulphate pulp was oxygen delignified and either bleached or unbleached. The kappa number of the pulp measured on-line after the oxygen delignification was between 8 and 11. The bleached reference fluff pulp was produced at the same fiber line, but this pulp was bleached in the bleaching plant to a kappa number of 1.

At the drying machine the pulp for trial point 2 and trial point 3 was treated with $Al_2(SO_4)_3$ and pH-adjusted with NaOH.

Fluff properties were tested according to the standard test methods. The results obtained are illustrated in table 1. The ISO Brightness was measured on the fluff pulp. The knot content, the specific volume, absorption time and absorption capacity were measured on the fluffed material, i.e. after defibration. The sheet and pulp properties were evaluated in controlled climate conditions according to ISO 187.

TABLE 3

Chemical and fluff properties

| Sample | Kappa number, wet pulp | $Al_2(SO_4)_3$ solution, l/BDt | ISO Brightness, % | Knot content, % | Specific volume, dry state, dm³/kg | Absorption time, s | Absorption capacity, g/g |
|---|---|---|---|---|---|---|---|
| Trial point 1 Oxygen delignified | 8-11 | 0 | 45-46 | 17-18* | 22 | 3.3-3.4 | 9.8 |
| Trial point 2 Oxygen delignified | 8-11 | 30 | 46-50 | 6-8* | 22-23 | 3.3-3.4 | 9.9-10.0 |
| Trial point 3 Oxygen delignified | 8-11 | 80 | 47-48 | 6-8** | 21 | 2.6-2.8 | 9.0-9.3 |
| Reference Bleached | 1 | 20 | 89-90 | 12* | 21 | 2.4 | 9.8 |

*Fluff defibretad in Kamas H01 hammer mill att 3600 rpm
**Fluff defibretad in Kamas H01 hammer mill att 2500 rpm It can be seen from the results reported in table 3 that the absorption properties as well as fluff properties (specific volume) are almost identical for the bleached fluff pulp as compared to the oxygen delignified fluff pulp.

In view of the above detailed description of the present invention, other modifications and variations will become apparent to those skilled in the art. However, it should be apparent that such other modifications and variations may be affected without departing from the spirit and scope of the invention.

The invention claimed is:

1. Fluff pulp having a Kappa number in a range of from 5 to 18 and having, when in a form of a dry sheet, an ISO brightness in a range of from 30 to 60% and having a specific volume in a dry defibrated state of at least 19 dm³/kg and having an absorption time in a range of from 2 to 4 seconds according to the standard SCAN-C 33:80, wherein at least 90% of fibers of the fluff pulp originate from softwood.

2. The fluff pulp according to claim 1, wherein the ISO brightness is in a range of from 30 to 40%.

3. The fluff pulp according to claim 1, wherein the ISO brightness is in a range of from 35 to 50%.

4. The fluff pulp according to claim 1, wherein the specific volume in the dry defibrated state is in a range of from 19 to 23 dm³/kg.

5. The fluff pulp according to claim 1, wherein the Kappa number is in a range of from 5 to 12.

6. The fluff pulp according to claim 1, wherein the ISO brightness is in a range of from 36 to 50%.

7. The fluff pulp according to claim 1, in a form of a roll.

8. A product comprising defibrated fluff pulp, wherein said defibrated fluff pulp comprises, prior to defibration, comprises the fluff pulp according to claim 1.

9. An airlaid nonwoven comprising defibrated fluff pulp wherein said defibrated fluff pulp comprises, prior to defibration, the fluff pulp according to claim 1.

10. An absorption core comprising defibrated fluff pulp, wherein said defibrated fluff pulp comprises, prior to defibration, the fluff pulp according to claim 1.

11. A hygiene product comprising the absorption core according to claim 10.

* * * * *